United States Patent [19]

Winn et al.

[11] 4,093,726
[45] June 6, 1978

[54] N-(2-BENZIMIDAZOLYL)-PIPERAZINES

[75] Inventors: Martin Winn, Deerfield; Jaroslav Kyncl, Lake Bluff, both of Ill.

[73] Assignee: Abbott Laboratories, North Chicago, Ill.

[21] Appl. No.: 746,657

[22] Filed: Dec. 2, 1976

[51] Int. Cl.² .................. C07D 401/04; A61K 31/495
[52] U.S. Cl. .................... 424/250; 260/347.3; 544/370
[58] Field of Search .......... 260/268 BC, 309.2; 424/250

[56] References Cited
U.S. PATENT DOCUMENTS

| | | | |
|---|---|---|---|
| 3,574,218 | 4/1971 | Hideg et al. | 260/293.59 |
| 3,822,267 | 7/1974 | Sorg et al. | 260/268 BC |
| 4,011,322 | 3/1977 | Rahtz et al. | 260/268 BC |

OTHER PUBLICATIONS

Thomas R. Herrin, et al., Chemical Abstracts, vol. 83, 201749p, (1975).

Primary Examiner—Jose Tovar
Attorney, Agent, or Firm—Gildo E. Fato; Robert L. Niblack

[57] ABSTRACT

Disclosed are compounds of the formula

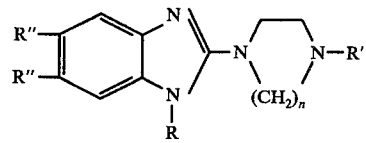

wherein $n$ is 2 or 3, R is hydrogen or methyl, R' is $C_1$-$C_6$ alkyl, acyl, aryl, aroyl, alkoxycarbonyl, tetrahydrofuroyl, dialkylaminocarbonyl, or furoyl, and R" is hydrogen and methoxy. These compounds are useful as antihypertensive agents.

13 Claims, No Drawings

N-(2-BENZIMIDAZOLYL)-PIPERAZINES

BACKGROUND OF THE INVENTION

Hypertension describes a symptom of several disease entities, both of known and unknown etiology, blood pressure being one measurement indicating its presence. There are two components of blood pressure, the systolic, which is the pressure produced by the pumping action of the heart and which has a normal measurement of between 120 and 140 ml. of mercury, and the diastolic pressure, which is the pressure due to the peripheral resistance of the blood vessels, normally having a value between 70 and 90 ml. of mercury. The systolic pressure is much more apt to be labile, varying with emotion and stress while the diastolic pressure is commonly more stable. A persistently elevated diastolic pressure is considered a serious symptom. Normal blood pressure varies with individuals, circumstances, and techniques used for measurement. Normal values also tend to rise during an individual's life time. High blood pressure can be temporary or can result from known causes such as kidney or artery disease. While some types of hypertension respond only to surgery and in others sedatives may comprise the sole therapy, most forms of hypertension are treated by means of chemotherapy. Chemical entities capable of lowering blood pressure in mammals are consequently highly desirable.

SUMMARY OF THE INVENTION

This invention relates to compounds of the formula

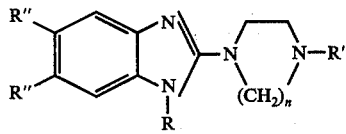

wherein $n$ is 2 or 3, R is hydrogen or methyl, R' is $C_1$-$C_6$ alkyl, acyl, aryl, aroyl, alkoxycarbonyl, tetrahydrofuroyl, dialkylaminocarbonyl, or furoyl, and R" is hydrogen and methoxy. The compounds of this invention are useful an anti-hypertensive agents and can be administered intraperitoneally or orally, for example. Further, they can be administered in time release form, if desired.

DETAILED DESCRIPTION

The compounds of the present invention can be prepared according to the following reaction schemes
(I) Il Farmaco 28 (2) P. 170

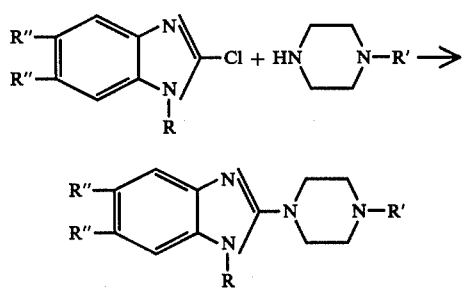

The starting chloro benzimidazoles are described in the following literature references:
I (R=H, R"=CH$_3$O) Il Farmaco 28 (2), 164 (1973)
((R=CH$_3$ R"=CH$_3$O) J. Org. Chem. USSR, 1, 1466 (1965)
I (R=H R"=H) J. Chem. Soc., 1963, 2930

EXAMPLE I 1-(5,6-Dimethoxy-2-benzimmidazolyl)-4-(2-furoyl) piperazine 2.02 g of 2. chloro-5,6-dimethoxy benzimidazolyl [(Lit. of Farmaco 28 (2) 164 (1970)] and 4.00 g N-(2-furoyl) piperazine (preparation described in Netherland Pat. No. 7,206,067) and 18 ml 2-methoxyethanol were refluxed 6½ hours. The solvent was removed in vacuo and the residue treated with 15 ml of a saturated solution of potassium bicarbonate in water. On cooling the product crystallized out and was recrystallized from isopropyl alochol and ethyl ether mixtures. Yield: 2.78 g. mp 143°–145° C.

Analysis for $C_{18}H_{20}N_4O_4$. Theory: C=60.66; H=5.66; N=15.72. Found: C=60.4; H=5.73; N=15.64.

Note: the synthesis of 4-(2-furoyl) piperazine is more fully described in copending patent application, Ser. No. 621,980; filed Oct. 14. 1975.

EXAMPLE II 4-(5,6-Dimethoxy-2-benzimidazolyl) piperazine-1-carboxylic ethyl ester Using the method of Example I. 4,80 g 2-chloro 5,6-dimethoxy benzemidazole, 8.00 g N-carbethoxy piperazine and 20 ml 2-methoxyethanol were reflexed 5½ hours to give 7.45 g (94%) of product mp, 114°–118° C.

Calculated for $C_{16}H_{22}N_4O_4$ ½ $H_2O$: C=56.00; H=6.75; N=16.33. Found: C=56.08; H=6.66; N=16.34.

EXAMPLE III 1-(5,6-Dimethoxy-1-methyl-2-benzimidazolyl)-4-(2-furoyl) piperazine hydrochloride 3.50 g. 2-chloro. 5,6-dimethoxy-1-methyl benzimidazole [(J. Org. Chem. USSR 1 1466), (1965)] 7.00 g N-(2-furoyl) piperazine, and 25 ml 2-methoxyethanol were reacted as described in Example I. The product was converted to its hydrochloride by dissolving in isopropyl alcohol and acidifying with a solution of HCl gas in isopropyl alcohol. Yield: 3.99 g product, mp 212°–215° C decomp.

EXAMPLE IV

N- (Tetrahydro-2-furoyl) piperazine

N-(2-furoyl) piperazine was converted to its hydro bromide salt (mp 173°–175° C). 39.0 g of this salt in 250 ml methanol and 9.0 g Rh catalyst was hydrogenated at 3 atm. After uptake of hydrogen ceased, the catalyst was filtered, the solvent concentrated and the residue crystallized from isopropyl alcohol to give 35.2 g N-(tetrohydro-2-furoyl) piperazine. HBr, mp 152°–156° C. This was suspended in 20 ml water. Then 10.5 g 50% NaOH was added slowly followed by 2.0 g solid Na$_2$CO$_3$. This mixture was extracted with four 100 ml. portions of warm chloroform. The chloroform extracts were distilled to give 22.5 g N-(tetrahydro-2-furoyl) piperazine bp 120°–125° C/0.2mm.

EXAMPLE V 1-(5,6-Dimethoxy-2-benzimidazolyl)-4(tetrahydro-2-furoyl) piperazine hydrochloride 3.00 g 2-chloro-5,6-dimethoxybenzimadazole, 6.50 g N-tetrahydro-2-furoyl) piperazine, and 30 ml methoxyethanol were refluxed 6¼ hours. The solvents were removed in vacuo and potassium bicarbonate solution added. This solution was extracted with $CHCl_3$, dried over magnesium sulfate, concentrated and ether was added to get the product. This was converted to the hydrochloride with HCl in isopropyl alochol. Yield: 4.74 g mp 253°–255° C (84%)

EXAMPLE VI 4-(5,6-Dimethoxy-2-benzimidazolyl) piperazine-1-carboxylic acid isobutyl ester-hydrochloride 3.40 g 2-chloro-5,6-dimethoxy benzimidazole, 7.50 g piperazine N-carboxylic acid isobutyl ester (described in U.S. 3,635,979, Example LVII) and 25 ml 2-methoxyethanol were reacted as in Example I to give the base of the desired product as a gum. This was washed free of starting amine with water, then dissolved in isopropyl alcohol and acidified with HCl gas to give 5.30 g product HCl salt, mp 248°–250° C (86%) Analysis for $C_{18}H_{26}N_4O_4H_2O$; C=52.00; H=6.78; N=13.45; Found: C=52.04; H=6.89; N=13.49.

EXAMPLE VII

N,N-Dimethyl 4-(5,6-dimethoxy-2-benzimidazolyl) piperazine-1-carboxamide hydrochloride 3.50 g 2-chloro 5,6-dimethoxybenzimidazole, 7.50 g N,N-dimethyl 1-piperazine carboxamide [J. Org. Chem. 13 144 (1948)], 20 ml methoxyethanol was reacted as described in Example I. The product was converted to the HCl salt with HCl in isopropyl alcohol. Yield: 5.33 g mp 252°–254° C (85%)

Analysis for $C_{16}H_{23}N_5O_3\cdot HCl\cdot 2H_2O$: C= 47.35; H=6.95; N=17.25; Cl=8.73. Found: C=47.61; H=6.83; N=17.18; Cl=8.87.

EXAMPLE VIII 1-(5,6-Dimethoxy-2-benzimidazolyl)-4(3,4-dimethoxyphenyl piperazine By the method of Example I, 3.00 g 2-chloro-5,6-dimethoxy-benzimidazole, 7.00 g N(3,4-dimethxoyphenyl) piperazine [J. Med. Chem. 10 812 (1967)] and 20 ml 2-methoxyethanol were reacted to give 4.21 g product, mp 209°–211° C as the base crystalized from $CHCl_3$-isopropyl alcohol) Analysis: Calculated for $C_{21}H_{16}N_4O_4$: C=63.30; H=6,58; H=14.06. Found: C=63.01; H=6.73; N=13.98.

EXAMPLE IX

N (4-methyl valeroyl) piperazine 60 g 4-methylvaleric acid was converted to the acid chloride by heating 1 hour with 120 g thionyl chloride. Distillation gave 45.2 g (65%) 4-methyl valeroyl chloride, bp 35°–38° C/10.0 mm. This product in 100 ml benzene was added to a solution of 56 g N-benzyl piperazine and 33.8 g triethylamine in 250 ml benzene. After 1 hour at 25° a solution of 47 g potassium carbonate in 250 ml water was added. The benzene layer was removed and concentrated. The crude N-(4-methyl valeroyl) N'-benzyl piperazine was hydrogenated in 300 ml ethanol using 16 g 5% pd/catalyst. The product was distilled to give 40.2 g product, bp 110°–115° C/0.1 mm. (65%)

EXAMPLE X 1-(5,6-Dimethoxy-2-benzimidazolyl)-4(4-methylvaleroyl) piperazine hydrochloride By the method of Example I, 2.00 g 2-chloro-5,6-dimethoxy benzimidazole and 4.00 g N-(4-methyl valeroyl) piperazine were reacted in 15 ml. 2-methoxy ethanol to give the desired product as a base; which was converted to the hydrochloride with HCl in isopropyl alcohol. Yield: 3.31 g (89%) mp 255°–257° C.

Analysis for $C_{19}H_{28}N_4O_3\cdot HCl$: C=57.49; H=7.36; N=14.11; Cl=8.93. Found C=57.20; H=7.51; N=13.98; Cl=8.63.

EXAMPLE XI 1-(5,6-dimethoxy-2-benzimidazolyl)-4(3-trifluoromethyl phenyl) piperazine hydrochloride By the method of Example I, 2.00 g 2-chloro-5,6-dimethoxy benzimidazole and 5.40 g N-(3-Trifluoromethyl phenyl) piperazine in 25 ml methoxyethanol gave the product as a base which was converted to the hydrochloride with HCl in methanol. Yield: 3.79 g (91%) mp 275° C.

Analysis for $C_{20}H_{21}F_3N_4O_2$: C=54.29; H=5.00; N=12.65; Cl=8.00. Found: C=54.64; H=4.90; N=12.56; Cl=8.01.

EXAMPLE XII

N-(2-Furoyl) homopiperazine

Homopiperazine (70 g) in 160 ml $H_2O$ was treated with hydrochloric acid (1 part conc. HCl and 1 part water) until the pH of the solution was 5.5. Furoyl chloride (79.5 g) and 25% NaOH was added simultaneously to maintain a pH between 4.5 and 5.5. Then 50% sodium hydroxide was added until the pH reached 9.5. The solution was extracted with chloroform, dried over potassium carbonate and distilled giving 63.24 g of product. bp 125°–130° C, 10.2mm.

Analysis theoretical for $C_{10}H_{14}N_2O_2$: C=61.83; H=7.27; N=14.42. Found C=61.57; H=7.39; N=14.30.

EXAMPLE XIII 1-(2-Furoyl)-4-(5,6-dimethoxy-2-benzimidazolyl) homopiperazine hydrochloride 2-chloro-5,6-dimethoxy benzimidazole (2.00 g) N-furoyl homopiperazine (4.20 g) in 20 ml -2 methoxy ethanol was refluxed 6.5 hours. The reaction mixture was worked up as described in Example I to give 700 mg product, mp 250°–251° C.

EXAMPLE XIV 1-methyl 4(2-benzimidazolyl) piperazine 2-chlorobenzimidazole (5.0 g) and piperazine (8.0 g) were dissolved in 10 ml isopropyl alcohol and refluxed 6.5 hours. The solution was concentrated in vacuo. The residue treated with sodium carbonate and then extracted with chloroform to yield 5.55 g product. mp. 222°–224° C.

Analysis calculated for $C_{12}H_{16}N_4$ C=66.64; H=7.46; N=25.91. Found C=66.68; H=7.56; N=25.80.

The antihypertensive effect of the compounds of the invention were screened in spontaneously hypertensive (SH) rats and found to be potent antihypertensive agents. The screening is conducted as follows:

Male spontaneously hypertensive (SH) rats are trained to be restrained in a wire mesh cylinder in a warming box, at least two training cycles being conducted before testing. The rats are warmed for about ½ hour period to blood pressure measurement, the warming box being maintained at a constant temperature of 36° C.

An occluding cuff attached to the programmed sphymamanometer is placed near the base of the tail of each rat and the pressure in the cuff is increased automatically from 0 to 250 milimeters of mercury (mm $H_g$) at a rate of 10 mm $H_g$ per second. The total time for each cycle of inflation and deflation of the cuff is 50 seconds and the interval between cycles is one minute.

A photocell is placed distal to the cuff to record the pulses due to forward motion of blood flow with each heart beat. As the pressure in the cuff increases, the pulse disappears completely at a point where cuff pressure equals or exceeds the arterial blood pressure and it reappears during deflation at approximately the same pressure. Five interference free signals for deflation are recorded for each rat. Rats with a blood pressure of 180 mm $H_g$ or more during the control period are used in the study. Blood pressure and heart rate readings are recorded on a model VII Grass polygraph at intervals of 1, 3, 5, and 24 hours after administration of the drug.

The data obtained is summarized in the following tables from which it is apparent that the compounds are potent antihypertensive agents which lower the blood pressure of spontaneously hypertensive rats.

As an example, the compound of Example VI produced a decrease in blood pressure of the magnitude of between 20 to 40% when administered intraperitoneally in the dose range from 10–30 mg/kg. The duration of the effect was greater than 5 hours at the dose of 30 mg/kg while the lowest dose of 10 mg/kg still caused an effect lasting for more than five hours. Likewise, when administered via the oral route, the compound caused a fall in blood pressure by up to approximately 35% when administered at a dose of 30 mg/kg.

| Cmpd. Ex. No. | n | R | R' | R" | Intra-Peritoneal Dose (mg/kg) | Percent Reduction In Blood Pressure In Two Rats At: | | | | Oral Dose, (mg/kg) | | | |
|---|---|---|---|---|---|---|---|---|---|---|---|---|---|
| | | | | | | 1 hr. | 3 hr. | 5 hr. | 24 hr. | | 1 hr. | 3 hr. | 5 hr. |
| I | 2 | H | $\underset{\text{C}-\text{O}}{\overset{\text{O}}{\parallel}}$ (furoyl) | $CH_3O$ | 30 | 39,37 | 28,32 | 33,34 | | 30 | | 13,25 | |
| II | 2 | H | $\text{C}(=\text{O})-\text{OCH}_2\text{CH}_3$ | $CH_3O$ | 30 | 18,13 | 20,22 | 20,25 | | 30 | 13,34 | 15,22 | 3,20 |
| III | 2 | $CH_3$ | furoyl | $CH_3O$ | 30 | 22,12 | 17,15 | 17,15 | | | | | |
| V | 2 | H | tetrahydrofuroyl | $CH_3O$ | 30 | 19,20 | 13,12 | 16,9 | | | | | |
| VI | 2 | H | $\text{C}(=\text{O})-\text{OCH}_2\text{CH}(\text{CH}_3)_2$ | $CH_3O$ | 30 | 36,38 | 21,20 | 24,29 | | 30 | 26,31 | 20,35 | 17,33 |
| | | | | | 10 | 32,47 | 27,40 | 22,35 | | | | | |
| VII | 2 | H | $\text{CN}(\text{CH}_3)_2\text{C}=\text{O}$ | $CH_3O$ | 30 | 14,6 | 14,7 | 16,4 | 19,15 | | | | |
| VIII | 2 | H | 2,6-dimethoxyphenyl | $CH_3O$ | 30 | 14,15 | 33,36 | 14,17 | 12,18 | 30 | 3,7 | 8,27 | 9,20 |
| X | 2 | H | $\text{C}(=\text{O})-\text{CH}_2\text{CH}_2\text{CH}(\text{CH}_3)_2$ | $CH_3O$ | 30 | 29,21 | 17,13 | 19,11 | | | | | |
| XIII | 3 | H | furoyl | $CH_3O$ | 30 | 31,34 | 17,18 | 16,15 | | | | | |
| XIV | 2 | H | $CH_3$ | H | 30 | 39,34 | 18,25 | 24,9 | | 30 | 14,21 | 7,23 | 5,15 |

What is claimed is:

1. A compound of the formula:

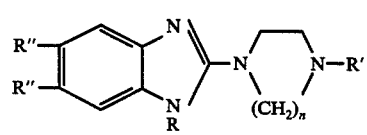

wherein:
n is 2;
R is selected from the group consisting of hydrogen or methyl;
R' is $C_1$-$C_6$ alkyl, 4-methyl valeroyl, phenyl, dimethoxyphenyl, $CF_3$-phenyl, tetrahydrofuroyl, Furoyl,

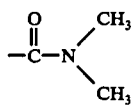

or $C_2$-$C_4$ alkoxy carbonyl and

R" is selected from the group consisting of hydrogen or methoxy.

2. A compound selected from the group consisting of 1-(5,6-Dimethoxy-2-benzimidazolyl)-4-(2-furoyl) piperazine, 4-(5,6-Dimethoxy-2-benzimidazolyl) piperazine-1-carboxylic ethyl ester, 1-(5,6-Dimethoxy-1-methyl-2-benzimidazolyl)-4-(2-furoyl) piperazine, 1-(5,6-Dimethoxy-2-benzimidazolyl)-4 (tetrahydro-2-furoyl) piperazine, 4-(5,6-Dimethoxy-2-benzimidazolyl) piperazine-1-carboxylic acid isobutyl ester, N,N-Dimethyl 4-(5,6-dimethoxy-2-benzimidazole piperazine-1-carboxamide, 1-(5,6-Dimethoxy-2-benzimidazolyl)-4 (3,4-dimethoxy-phenyl) piperazine, 1-(5,6-Dimethoxy-2-benzimidazolyl)-4(4-methylvaleroyl) piperazine, 1-(5,6-Dimethoxy-2-benzimidazolyl)-4(3-trifluoromethyl phenyl) piperazine, 1-methyl 4(2-benzimidazolyl) piperazine and pharmaceutically acceptable acid addition salts thereof.

3. A compound selected from the group consisting of: 1-(5,6-Dimethoxy-2-benzimidazolyl)-4-(2-furoyl) piperazine, 4-(5,6-Dimethoxy-2-benzimidazolyl) piperazine-1-carboxylic ethyl ester, 4-(5,6-Dimethoxy-2-benzimidazolyl) piperazine-1-carboxylic acid isobutyl ester, and 1-(5,6-Dimethoxy-2-benzimidazolyl)-4(3,4-dimethoxy-phenyl) piperazine.

4. A compound in accordance with claim 3; 4-(5,6-Dimethoxy-2-benzimidazolyl) piperazine-1-carboxylic ethyl ester.

5. A compound in accordance with claim 3; 4-(5,6-Dimethoxy-2-benzimidazolyl) piperazine-1-carboxylic acid isobutyl ester-hydrochloride.

6. An antihypertensive pharmaceutical composition comprising a compound selected from the group consisting of 1-(5,6-Dimethoxy-2-benzimidazolyl)-4-(2-furoyl) piperazine, 4-(5,6-Dimethoxy-2-benzimidazolyl) piperazine-1-carboxylic ethyl ester, 1-(5,6-Dimethoxy-1-methyl-2-benzimidazolyl)-4-(2-furoyl) piperazine, 1-(5,6-Dimethoxy-2-benzimidazolyl)-4 (tetrahydro-2-furoyl) piperazine, 4-(5,6-Dimethoxy-2-benzimidazolyl) piperazine-1-carboxylic acid isobutyl ester, N,N-Dimethyl 4-(5,6-dimethoxy-2-benzimidazolyl) piperazine-1-carboxamide, 1-(5,6-Dimethoxy-2-benzimidazolyl)-4(3,4-dimethoxy-phenyl) piperazine, N (4-methyl valeroyl) piperazine, 1-(5,6-Dimethoxy-2-benzimidazolyl)-4(4-methylvaleroyl) piperazine, 1-(5,6-Dimethoxy-2-benzimidazolyl)-4(3-trifluoromethyl phenyl) piperazine, 1-methyl 4(2-benzimidazolyl) piperazine and pharmaceutically acceptable acid addition salts thereof and a pharmaceutically acceptable carrier.

7. A composition of claim 6 wherein the compound is selected from the group consisting of 1-(5,6-Dimethoxy-2-benzimidazolyl)-4-(2-furoyl) piperazine, 4-(5,6-Dimethoxy-2-benzimidazolyl) piperazine-1-carboxylic ethyl ester, 4-(5,6-Dimethoxy-2-benzimidazolyl) piperazine-1-carboxylic acid isobutyl ester, and 1-(5,6-Dimethoxy-2-benzimidazolyl)-4(3,4-dimethoxy-phenyl) piperazine and pharmaceutically acceptable acid addition salts thereof.

8. The composition of claim 7 wherein the compound is 4-(5,6-dimethoxy-2-benzimidazolyl) piperazine-1-carboxylic ethyl ester and pharmaceutically acceptable acid addition salts thereof.

9. The composition of claim 7 wherein the compound is 4-(5,6-dimethoxy-2-benzimidazolyl) piperazine-1-carboxylic acid isobutyl ester and pharmaceutically acceptable acid addition salts thereof.

10. A method of treating hypertension in a mammal comprising administering to a mammal so afflicted a therapeutically effective amount of a compound selected from the groups consisting of: 1-(5,6-Dimethoxy-2-benzimidazolyl)-4-(2-furoyl) piperazine, 4-(5,6-Dimethoxy-2-benzimidazolyl) piperazine-1-carboxylic ethyl ester, 1-(5,6-Dimethoxy-1-methyl-2-benzimidazolyl)-4-(2-furoyl) piperazine, 1-(5,6-Dimethoxy-2-benzimidazolyl)-4 (tetrahydro-2-furoyl) piperazine, 4-(5,6-Dimethoxy-2-benzimidazolyl) piperazine-1-carboxylic acid isobutyl ester, N,N-Dimethyl 4-(5,6-dimethoxy-2-benzimidazolyl) piperazine-1-carboxamide, 1-(5,6-Dimethoxy-2-benzimidazolyl)-4(3,4-dimethoxy-phenyl) piperazine, 1-(5,6-Dimethoxy-2-benzimidazolyl)-4(4-methylvaleroyl) piperazine, 1-(5,6-Dimethoxy-2-benzimidazolyl)-4(3-trifluoromethyl phenyl) piperazine, 1-methyl 4(2-benzimidazolyl) piperazine and pharmaceutically acceptable acid addition salts thereof.

11. The method of claim 10 wherein said compound is 4-(5,6-Dimethoxy-2-benzimidazolyl) piperazine-1-carboxylic ethyl ester.

12. The method of claim 10 wherein said compound is 4-(5,6-dimethoxy-2-benzimidazolyl) piperazine-1-carboxylic acid isobutyl ester-hydrochloride.

13. A compound of the formula:

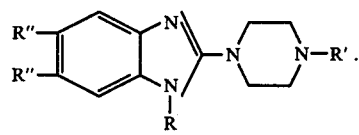

wherein:

R is selected from the group consisting of hydrogen or methyl;

R' is $C_2$-$C_4$ alkoxy carbonyl or N,N-dimethylamino carbonyl and

R" is selected from the group consisting of hydrogen or methoxy.

* * * * *